United States Patent [19]

Marx et al.

[11] 4,181,720
[45] Jan. 1, 1980

[54] CORTICOSTEROID ANTIINFLAMMATORY AGENTS

[75] Inventors: Michael Marx, Sunnyvale; Denis J. Kertesz, Mountain View, both of Calif.

[73] Assignee: Syntex (U.S.A.) Inc., Palo Alto, Calif.

[21] Appl. No.: 893,631

[22] Filed: Apr. 5, 1978

[51] Int. Cl.² ............... A61K 31/58; A61K 31/56; C07J 71/00
[52] U.S. Cl. ................... 424/241; 424/243; 260/239.55 D; 260/397.45
[58] Field of Search ............ /Steroids MS File; 260/239.55 D, 397.45

[56] References Cited

U.S. PATENT DOCUMENTS

| 3,944,577 | 3/1976 | Laurent et al. | 260/397.1 |
| 4,011,315 | 3/1977 | Marx et al. | 260/239.55 D |

Primary Examiner—Elbert L. Roberts
Attorney, Agent, or Firm—Richard J. Hammond; Gerard A. Blaufarb

[57] ABSTRACT

22-Optionally substituted steroids of the corticoid series are prepared from the corresponding 21-methylene steroids through the 20,21-dione steroid intermediates. These compounds have utility as anti-inflammatory agents.

41 Claims, 1 Drawing Figure

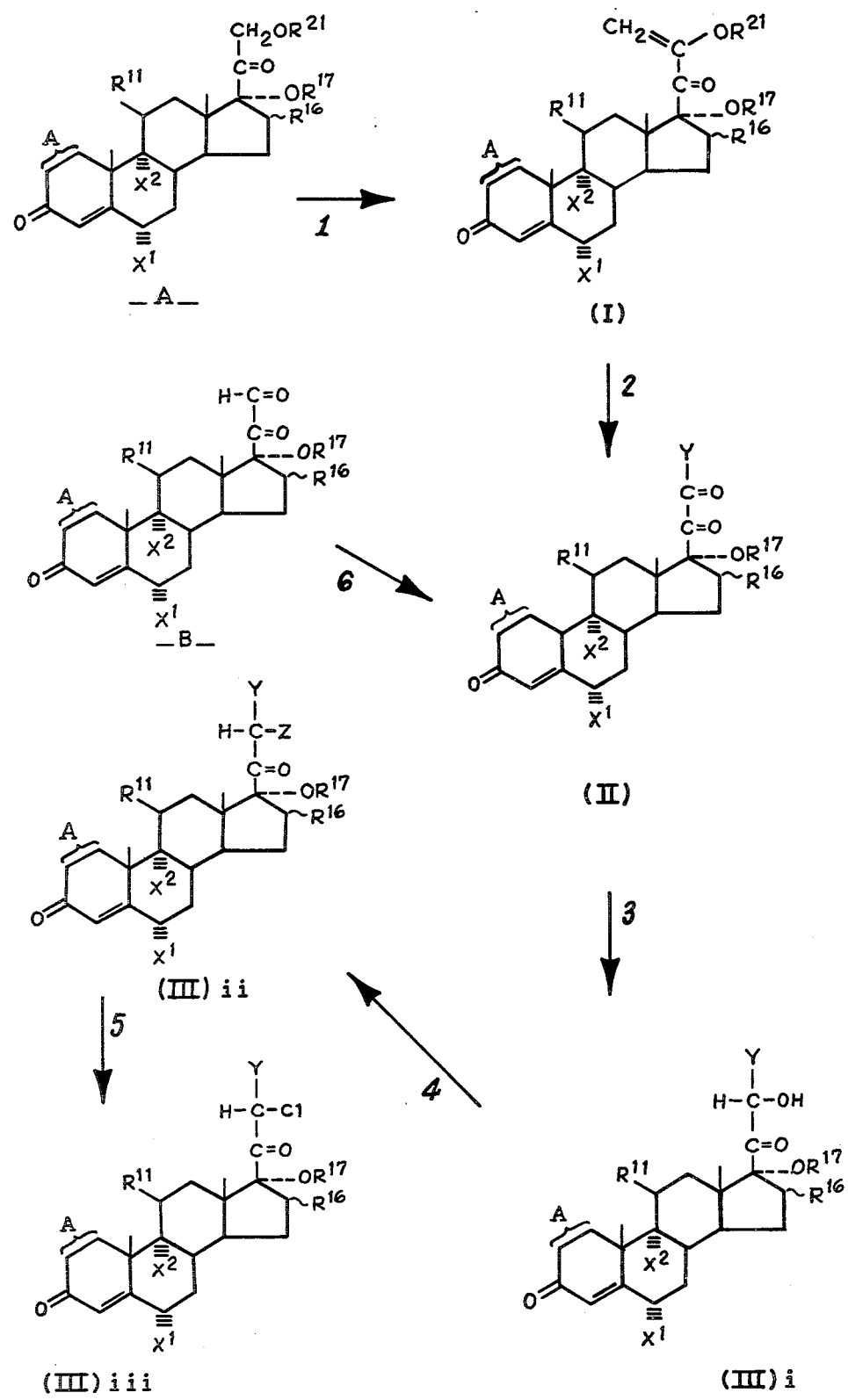
FIG_1

CORTICOSTEROID ANTIINFLAMMATORY AGENTS

SUMMARY

The present invention relates to cyclopentanophenanthrene derivatives and to certain novel compounds obtained as intermediates. More particularly, the present invention relates to novel compositions and methods utilizing compounds of the formula

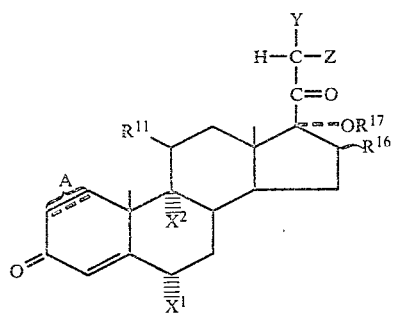

wherein
$R^{11}$ is chloro or hydroxy;
$X^1$ and $X^2$ independently are halo selected from the group chloro and fluoro;
$R^{16}$ is methyl;
$R^{17}$ independently is hydrogen, benzoyl optionally substituted with 1 to 3 substituents, the substituents being $C_1$ to $C_4$ linear or branched alkyl, halo, hydroxy or $C_1$ to $C_4$ linear or branched alkoxy or $C_2$ to $C_6$ linear or branched acyl, or $R^{16}$ and $OR^{17}$ taken together are the radical

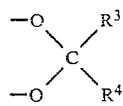

where $R^3$ is hydrogen, $C_1$ to $C_5$ linear or branched alkyl, phenyl optionally substituted with 1 to 3 substituents, the substituents being $C_1$ to $C_4$ linear or branched alkyl, halo, hydroxy or $C_1$ to $C_4$ linear or branched alkoxy and $R^4$ is the same or different than $R^3$ as defined above or is $C_1$ to $C_6$ linear or branched alkoxy or $R^3$ and $R^4$ taken together with the carbon atom of said radical are optionally substituted $C_5$ to $C_{10}$ cycloalkyl or optionally substituted $C_4$ to $C_9$ heterocyclic alkyl having at least one heterocyclic atom selected from the group oxygen, nitrogen and sulfur, preferably oxygen, the substituents being $C_1$ to $C_4$ linear or branched alkyl, halo, hydroxy or $C_1$ to $C_4$ linear or branched alkoxy;
Y is selected from the group methyl, halomethyl, and the radical —$CH_2OC(O)R$ where R is $C_1$ to $C_6$ linear or branched alkyl;
Z independently is $C_2$ to $C_7$ linear or branched acyloxy, hydroxy or halo, or Z and $OR^{17}$ taken together are the radical

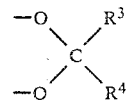

where $R^3$ and $R^4$ are defined above; and A is a double or single bond. The compositions herein contain novel compounds of formula (III) such that when Z independently is $C_2$ to $C_7$ linear or branched acyloxy or hydroxy, Y is selected from the group halomethyl and the radical —$CH_2OC(O)R$ where R is as previously defined with the proviso that when Y is methyl Z is halo.

A preferred subclass of compounds within the class defined by Formula (III) are the compounds where Z is hydroxy, halo selected from the group chloro and bromo, or $C_2$ to $C_4$ linear or branched acyloxy, and $R^{17}$ is $C_2$ to $C_5$ linear or branched acyl, benzoyl or $OR^{17}$ taken with either
$R^{16}$ or with Z form the radical

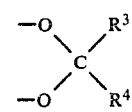

where, preferably, $R^3$ is $C_1$ to $C_4$ linear or branched alkyl and $R^4$ is the same as $R^3$ or is $C_1$ to $C_4$ linear or branched alkoxy. Particularly preferred compounds of Formula (III) are those where Y is methyl, or the radical —$CH_2OC(O)R$ where R is $C_1$ to $C_4$ linear or branched alkyl, $OR^{17}$ is taken together with Z to form the radical

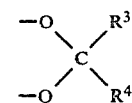

where $R^3$ is $C_1$ to $C_4$ linear or branched alkyl and $R^4$ is $C_1$ to $C_4$ linear or branched alkoxy, $X^1$ is the same as $X^2$ and is fluoro and A is a double bond. Other particularly preferred compounds of Formula (III) are those where Y is methyl, chloromethyl or the radical —$CH_2OC(O)R$ where R is $C_1$ to $C_4$ linear or branched alkyl, Z is acetoxy or chloro, $R^{17}$ is the $C_2$ to $C_4$ linear or branched acyl, $X^1$ and $X^2$ are the same and are fluoro and A is a double bond. Compounds of Formula (III) where Y is methyl, Z is chloro, $R^{16}$ and $OR^{17}$ are taken together to form the radical

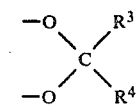

where $R^3$ is the same as $R^4$ and is $C_1$ to $C_4$ linear or branched alkyl, $X^1$ is the same as $X^2$ and is fluoro and A is a double bond are also particularly preferred.

In addition, the present invention relates to compounds obtained as intermediates in the preparation of compounds of Formula (III) and exhibiting similar pharmacological activity. These novel intermediates are represented by the formulas:

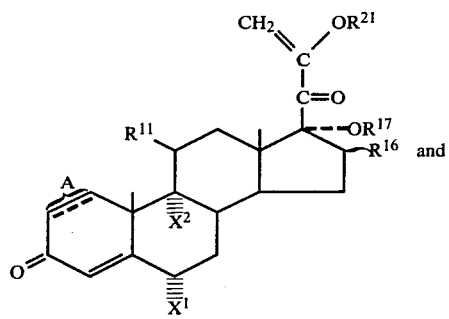 (I)

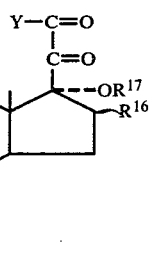 (II)

where A, $X^1$, $X^2$, $R^{11}$ $R^{16}$, $R^{17}$ and Y are as previously defined and $R^{21}$ independently is $C_1$ to $C_6$ linear or branched alkyl or optionally substituted $C_4$ to $C_9$ heterocyclic alkyl having at least one heterocyclic atom selected from the group oxygen, nitrogen, and sulfur, preferably oxygen, the substituents being $C_1$ to $C_4$ linear or branched alkyl, halo, hydroxy or $C_1$ to $C_4$ linear or branched alkoxy or $OR^{17}$ and $OR^{21}$ taken together are the radical

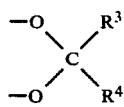

where $R^3$ is as previously defined and $R^4$ is $C_1$ to $C_6$ linear or branched alkoxy, with the proviso that when $R^{17}$ is hydrogen Y is selected from the group halomethyl and the radical $-CH_2OC(O)R$ where R is as previously defined.

A preferred subclass of compounds within the class defined by Formula (II) are those compounds where $R^{17}$ is $C_2$ to $C_4$ linear or branched acyl or benzoyl or those where $R^{16}$ and $OR^{17}$ are taken together to form the radical

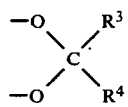

preferably where $R^3$ and $R^4$ are the same and are $C_1$ to $C_4$ linear or branched alkyl. Particularly preferred compounds in accordance with the present invention of Formula (II) are those where Y is selected from the group methyl, chloromethyl, bromomethyl and acetoxymethyl, $R^{17}$ is acetoxy or $R^{16}$ and $OR^{17}$ are taken together to form the radical

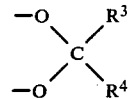

where $R^3$ and $R^4$ are the same and are methyl, $X^1$ is the same as $X^2$ and is fluoro and A is a double bond.

The preferred compounds of the present invention as defined by formula (I) are those compounds wherein $OR^{17}$ and $OR^{21}$ are taken together to form the radical

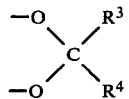

where $R^3$ is $C_1$ to $C_4$ linear or branched alkyl and $R^4$ is $C_1$ to $C_4$ linear or branched alkoxy or where $R^{16}$ and $OR^{17}$ are taken together to form the radical

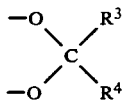

wherein $R^3$ is the same as $R^4$ and is $C_1$ to $C_4$ linear or branched alkyl or where $R^{21}$ is $C_1$ to $C_4$ linear or branched alkyl or $C_5$ to $C_{10}$ heterocyclic alkyl having 1 heterocyclic atom that is oxygen. Particularly preferred compounds of Formula (I) are those where $OR^{17}$ and $OR^{21}$ form the radical

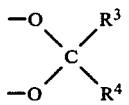

where $R^4$ is $C_1$ to $C_4$ linear or branched alkoxy or where $OR^{16}$ and $OR^{17}$ form the radical

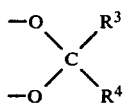

where $R^3$ is the same as $R^4$ and is methyl or where $R^{21}$ individually is methyl or tetrahydropyran-2-yl, $X^1$ is the same as $X^2$ and is fluoro and A is a double bond.

The method(s) of preparation of the compounds of the present invention are more readily apparent from the following description in connection with the accompanying drawing in which:

FIG. 1 is an illustration of the preferable reaction route to the compounds of the present invention.

DESCRIPTION OF THE PREFERRED EMBODIMENTS

The present invention is directed to the compounds illustrated in FIG. 1, Formulas (I), (II), and (III) and to methods for their preparation.

Referring to the drawing of FIG. 1, $R^{11}$, $X^1$, $X^2$, $R^{16}$, $R^{17}$, $R^{21}$, Y, Z, and A are as previously defined. Preferred starting compounds for preparing the materials of the present invention are those steroids of the pregnene series having the general formula A shown in FIG.

1. The presence of the carbonyl group at C-20 apparently activates the C-21 carbon atom to an extent sufficient so as to allow it to enter into further reactions. Thus, in the presence of a mildly strong base various groups can be introduced at the C-21 position. Such groups include the alkylidene group which may arise from the condensation of an appropriate aldehyde or ketone at the C-21 position to give use to an intermediate alcohol, typically followed by a spontaneous dehydration. In forming the compounds of the present invention of Formula (I), e.g., reaction step 1 in which $OR^{21}$ and $R^{17}$ taken together form the radical

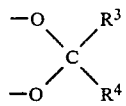

where $R^3$ is as previously defined and $R^4$ is the same as $R^3$ or is $C_1$ to $C_6$ linear or branched alkoxy or where $R^{21}$ is $C_1$ to $C_6$ linear or branched alkyl and $R^{16}$ and $OR^{17}$ are taken together to form the radical

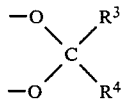

where $R^3$ is the same or different than $R^4$ and is as previously defined, a carbonyl reactant in the presence of a base is added to the C-21 position of compound A. While the carbonyl reactants of use herein may include aliphatic ketones, such as acetone, methyl ethyl ketone, 3-pentanone and the like, cycloaliphatic ketones such as cyclohexanone, cyclopentanone and the like, or aromatic ketones such as propiophenone, benzophenone and the like, aldehydes are the preferred reactants for condensation with the compounds of Formula A. Particularly preferred to form the compounds of the present invention is the reaction of compound A with formaldehyde so as to form a C-21 methylenic pregnene, such illustrated by the compound of the present invention of Formula (I). In cases where the previously mentioned C-21 intermediate is isolated, further reaction with organic carboxylic acids and chlorides and the like affords the 21a-carboxylates, i.e., compounds of formula (II) where Y is the radical $-CH_2OC(O)R$ where R is as previously defined.

The reaction of formaldehyde with the compound of Formula A is carried out in a non-reactive polar organic solvent, typically over a period of 2 to 24 hours at between 60° and 120° C. Preferably the solvent of use herein is a protic solvent such as illustrated by aqueous solutions of methanol, ethanol and the like. While any of a wide variety of base catalysts can be employed to promote the addition of the carbonyl reactants to the compounds of Formula A, bases of very low $pK_b$ should be avoided since such may cause undesirable reactions at other positions of the steroid nucleus. As such, sodium bicarbonate is most preferably used as the base catalyst herein.

The compounds of the present invention of Formula (I) are readily converted to the compounds of the present invention of Formula (II) by an acid catalyzed hydration at the double bond of the C-21 methylenic group (see illustrative reaction step 2). The resulting, typically unstable but isolable, 21-hydroxy intermediates sometimes referred to as a hemiacetal (not shown) readily lose water, affording the 21-methyl-20,21-dione, i.e., the compounds of Formula (II). Where $OR^{17}$ and $OR^{21}$ are taken together to form the radical

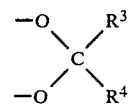

where $R^3$ is defined above and $R^4$ is $C_1$ to $C_4$ linear or branched alkoxy, the reaction yields compounds of Formula (II) where $R^{17}$ is $C_2$ to $C_6$ linear or branched acyl. When the above compounds of Formula (I) are reacted with a hypohalous acid, the corresponding, typically unstable, but isolable 21-hydroxy halohydrins are formed. These compounds also readily dehydrate to give compounds of the present invention where Y is halomethyl. Where $OR^{17}$ and $OR^{21}$ are taken together to form the radical

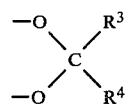

where $R^3$ is defined above and $R^4$ is $C_1$ to $C_6$ linear or branched alkoxy, the reaction in the presence of the cosolvent, yields compounds of Formula (II) where $R^{17}$ is $C_2$ to $C_6$ linear or branched acyl. Displacement of the 21a-halide by an anion of an alkali or alkaline earth metal carboxylate salt in an appropriate solvent affords the 21a-carboxylic ester, i.e., compounds of Formula (II) where Y is the radical $-CH_2OC(O)R$ where R is as previously defined.

In carrying out the hydration reaction as set forth above and as illustrated in FIG. 1, step 2, typically an aqueous organic solvent-containing solution of the 21-methylene compound of Formula (I), and an acid catalyst is heated at 20° to about 120° C., preferably 20° to 80° C. for from about 10 minutes to about 48 hours, preferably about 30 minutes to about 24 hours. A variety of acid catalysts are useful in accomplishing this reaction and as such include the organic carboxylic acids such as, para-toluene sulfonic acid, acetic acid and the like. Preferably 70% formic acid is used as the organic carboxylic acid. Inorganic mineral acids such as sulfuric acid, hydrochloric acid and the like, preferably dilute sulfuric acid (10% $H_2SO_4$ in water) can be employed in catalyzing the reaction of step 2 where Y is methyl in Formula (II). In the hypohalous acid reaction it is not necessary to add any other catalytic species. Typically, however, the hypohalous acid, or reagent solution generating the hypohalous acid is used in the presence of a strong mineral acid such as 5% sulfuric acid. The hydration reaction illustrated by step 2 of FIG. 1 of the C-21 methylene pregna-1,4-dienes is generally set forth in Tanabe et al, Chem. Pharm. Bull., 23 (11) 2728-2734 (1975) and in the Examples herein.

Alternately, the compounds of the present invention of Formula (II) where Y are methyl are readily prepared by reacting the 21-aldehyde (FIG. (I) step 6) compound B by an insertion reaction with diazomethane in an inert organic solvent. Surprisingly, the 21-methylpregna-1,4-diene-20,21 dione is obtained. The reaction is advantageously conducted in diethyl ether at about 0° to about 25° C. for from about 30 minutes to about 48 hours.

The 20,21-dione pregnadienes illustrated in FIG. 1 Formula (II) are readily converted to the compounds of the present invention of Formula (III) where Y is methyl, halomethyl or the radical —CH$_2$OC(O)R where R is as previously defined and Z is hydroxy by the selective reduction of the C-21 keto group. Preferably this reduction is accomplished by non-catalytic techniques utilizing sodium borohydride in a protic solvent such as methanol for about 30 minutes to about 3 hours at about 0° to about 20° C. It should be noted however that a number of other reducing agents are recognized by those skilled in the art as being sufficiently selective to effect the reduction at the C-21 keto group. As such, lithium aluminum hydride, lithium tri-t-butoxy aluminum hydroxide, potassium borohydride, lithium borohydride, sodium trimethoxyborohydride, diborane, aluminum isopropoxide in alcohol and the like may also be used in this reaction illustrated in FIG. 1, step 3.

The compounds of the present invention wherein Y is hydroxy and $R^{16}$ is methyl, i.e., the 16-methyl-21-hydroxy pregnadienes, are converted to their analogous 21-esters, 17 alpha,21-orthoesters, and 17-alpha, 21-ketals as shown in FIG. I, step 4 and as set forth in U.S. Pat. Nos. 3,116,289 or 3,280,159 incorporated herein by reference. Briefly, the 16,21-dimethyl-17,21-hydroxypregna-1,4-dienes are treated with a gem-dimethoxy $C_1$ to $C_6$ linear or branched alkane (to form the 17 alpha, 21-ketal), a $C_2$ to $C_6$ carboxylic acid chloride, carboxylic acid or carboxylic acid anhydride (to form the 21-esters) or an orthoester (to form the 17 alpha, 21-orthoester) typically in the presence of an acid catalyst. A more complete description of this method for preparing and isolating the compounds of the present invention of Formula (III)i where $R^{21}$ is $C_2$ to $C_6$ linear or branched acyl or where $OR^{17}$ and $OR^{21}$ taken together form the radical

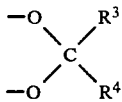

where $R^3$ is $C_1$ to $C_5$ linear or branched alkyl and $R^4$ is $C_1$ to $C_6$ linear or branched alkoxy and where $R^{16}$ is methyl or $R^{16}$ and $OR^{17}$ taken together form the radical

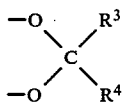

where $R^3$ is hydrogen, $C_1$ to $C_6$ linear or branched alkyl, phenyl optionally substituted with 1 to 3 substituents, the substituents being $C_1$ to $C_4$ linear or branched alkyl, halo, hydroxy, or $C_1$ to $C_4$ linear or branched alkoxy and $R^4$ is the same or different than $R^3$ as defined above or is $C_1$ to $C_6$ linear or branched alkoxy or $R^3$ and $R^4$ taken together with the carbon atom of said radical are optionally substituted $C_5$ to $C_{10}$ cycloalkyl or optionally substituted $C_4$ to $C_9$ heterocyclic alkyl having at least one heterocyclic atom selected from the group oxygen, nitrogen and sulfur, the substituents being $C_1$ to $C_4$ linear or branched alkyl, halo, hydroxy or $C_1$ to $C_4$ linear or branched alkoxy can be had by referring to the Examples herein. The compounds of the present invention of Formula (III)iii where Z is halo can be synthesized from the compounds of the present invention of Formula (III)ii where Z is taken together with $OR^{17}$ to form the radical

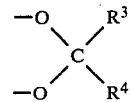

where $R^3$ is as previously defined and $R^4$ is $C_1$ to $C_4$ linear or branched alkoxy by reaction with a triarylmethylhalide, preferably triphenylmethylchloride in an inert organic solvent, preferably an inert non-polar organic solvent such as methylene chloride. (FIG. I, reaction step 5). Typically, this reaction is carried out at room temperature to about 50° C. for about 30 minutes to about 48 hours. The compounds formed from this reaction are the compounds of Formula (III) where Z is halo and $R^{17}$ is $C_2$ to $C_6$ linear or branched acyl. By an alternate process, compounds of Formula (III)iii where Z is halo but where $R^{16}$ and $OR^{17}$ are taken together to form the radical

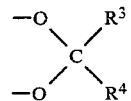

where $R^3$ and $R^4$ are as previously defined are formed by first substituting for the 21-hydroxy, e.g., the compounds of Formula (III)i where Z is hydroxy, a group that is a leaving group. Various readily displaceable (leaving) groups of the type are well-known in the prior art and are preferably the tosyl (para-toluenesulfonyl) and mesyl (methanesulfonyl) groups herein. The substitution of a leaving group for a hydroxy group in steroid reactions and in general organic reactions is described in detail in Fieser and Fieser, Reagents for Organic Synthesis, John Wiley & Sons Inc., 1967, for example page 662, and in the Examples herein. Displacement of the 21-leaving group substituted pregna-1,4-dienes is accomplished at elevated temperatures. Such displacement is preferably conducted at from about 75° to about 175° C., preferably 120° to 140° C. for about 30 minutes to about 48 hours in an inert polar organic solvent. The solvent is selected so as to dissolve both the leaving group-substituted pregnadiene and the halogen source, typically a halide salt such as sodium chloride, potassium chloride, lithium bromide, lithium iodide, and the like, preferably lithium chloride.

Alternately, the compounds of the present invention of Formula (III)ii where Z is the radical OC(O)R where R is defined above can be formed from the compounds of the present invention of Formula (III)i by a simple esterification reaction preferably using an acid chloride in the presence of an acid acceptor. Such esterifications are well known in the prior art and are described in for example Steroid Reactions, C. Djerassi, Ed., Holden-Day Inc., 1963, and illustrated in the Examples herein.

The compounds of the present invention are potent topical anti-inflammatory agents. Although the instant compounds exhibit low systemic activity in the rat as measured in standard assays, e.g. Rat Thymoltic Assay, they exhibit high topical activity in humans as measured in the Stoughton-McKenzie Assay (Human Vasoconstrictor Assay). In spite of the fact that systemic effects such as adrenal atrophy, mineralocorticoid effects and collagen disorders may be produced by large doses of the instant compounds if administered or long periods of time, the favorable topical/systemic activity ratio of the instant compounds permits the use of such small doses that these systemic effects are minimized. This combination of high topical anti-inflammatory activity coupled with negligible systemic activity renders the instant compounds highly suitable for the alleviation of inflammatory disorders.

The present invention further relates to a method for treating symptoms associated with inflammatory disorders, which method comprises administering an effective amount of a compound selected from those represented by formulas (I), (II) and (III), or a pharmaceutical composition incorporating such compound(s) as an active ingredient.

The present invention still further relates to pharmaceutical compositions useful for treating inflammatory disorders. These compositions comprise an effective amount of a compound selected from those represented by Formulas (I), (II) and (III) in admixture with a pharmaceutically acceptable, non-toxic carrier.

Suitable carriers or medicament vehicles for topical application of the steroids of the instant invention include creams, ointments, lotions, emulsions, solutions, and the like. For example, a suitable ointment for topical application of compounds of the instant invention contains 15 to 45 percent of a saturated fatty alcohol having 16 to 24 carbon atoms such as cetyl alcohol, stearyl alcohol, behenyl alcohol, and the like and 45 to 85 wt. percent of a glycol solvent such as propylene glycol, polyethylene glycol, dipropylene glycol, and mixtures thereof. The ointment can also contain 0 to 15 wt. percent of a plasticizer such as polyethylene glycol, 1,2,6-hexanetriol, sorbitol, glycerol, and the like; 0 to 15 wt. percent of a coupling agent such as a saturated fatty acid having from 16 to 24 carbon atoms, e.g., stearic acid, palmitic acid, behemic acid, a fatty acid amide e.g., oleamide, palmitamide, stearamide, behenamide and an ester of a fatty acid having from 16 to 24 carbon atoms such as sorbitol monostearate, polyethylene glycol monostearate, polypropylene glycol or the corresponding mono-ester of other fatty acids such as oleic acid and palmitic acid; and 0 to 20 wt. percent of a penetrant such as dimethyl sulfoxide, dimethylacetamide, dimethylformamide, and the like.

The concentration of cortical steroid in pharmaceutical compositions suitable for topical application will vary depending upon the particular activity of the steroid used in conjunction with the condition and subject to be treated. In general, topical preparations containing 0.005 to 1% by weight of the active steroid are advantageously employed.

In the specification and claims the following definitions apply:

The wavy line ($\sim$) used in the depicted formulas indicates that the substituent attached to those positions can be in either the (alpha) or (beta) configuration.

The broken line (≡) used in the depicted formulas indicates that the substituent attached to those positions is in the alpha configuration.

The unbroken line (—) used in the depicted formulas indicates that the substituent attached to those positions is in the beta configuration.

The term "$C_1$ to $C_5$ linear or branched alkyl" defines aliphatic hydrocarbons containing from 1 to 5 carbon atoms including all isomers thereof. Typically these groups are methyl, ethyl, n-propyl, isopropyl, n-butyl, sec-butyl, n-amyl, 2-methylbutyl, and so forth. Similarly the term "$C_1$ to $C_4$ linear or branched alkyl" defines those aliphatic hydrocarbons of 1 to 4 carbon atoms.

The term "$C_2$ to $C_7$ linear or branched acyloxy" refers to those esters employed in the cortical steroid art having from 2 to 7 carbon atoms including the radical

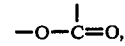

i.e., being derived from alkanoic or phenyl carboxylic acids. Typical acyloxy groups expressed as the ester include for example acetate, propionate, butyrate, valerate, benzoate and the like.

Similarly, the term "$C_2$ to $C_6$ acyl" refers to those aliphatic hydrocarbons bearing the radical

and having from 2 to 6 carbon atoms including all isomers thereof. Typical acyl groups are acetyl, propionyl, n-butyroyl and the like.

"$C_5$ to $C_{10}$ cycloalkyl" is intended to mean the 5 to 10 carbon cyclic compounds such as cyclopentane, cyclohexane, methylcyclopentane and the like. Similarly "$C_4$ to $C_9$ heterocyclic alkyl having at least one heterocyclic atom selected from the group nitrogen, oxygen and sulfur" defines the saturated heterocyclics of 4 to 9 carbon atoms containing preferably one heteroatom, i.e. tetrahydrofuran, pyrrolidine, pyran, tetrahydrothiophene and the like optionally substituted with the groups methyl, ethyl and the like.

Compounds of Formula (III) wherein Y and Z are not identical exist in two epimeric forms, i.e., the 21(R) and 21(S) forms. Accordingly, all nomenclature, formula and discussion herein is intended to refer to both forms and mixtures thereof unless otherwise specified. In some illustrative Examples herein, the pure epimeric compounds are set forth but absolute configurations are unknown, i.e., the alpha or beta epimeric compounds. As such, the compounds are identified as the Epimer A or Epimer B to denote a pure epimeric form but unidentified as to configuration.

EXAMPLE 1

6 Alpha,9 alpha-difluoro-11 beta,17 alpha,21-trihydroxy-16 alpha-methyl-21-methylenepregna-1,4-diene-3,20-dione-17,21-methyl orthoacetate.

(a) A mixture of 6 alpha,9 alpha-difluoro-11 beta,17 alpha,21-trihydroxy-16-alpha-methylpregna-1,4-diene-3,20-dione (flumethasone) (1 g) and para-toluenesulfonic acid monohydrate (0.5 g) in trimethyl orthoacetate (20 ml) and benzene (30 ml), is slowly distilled (90° C. bath) to remove water azeotropically until thin layer chromatography indicates that no starting material remains. The reaction mixture is evaporated to dryness, the residue slurried in benzene and filtered. The material is isolated by filtration and is recrystallized from methanol/methylene chloride to give 6 alpha,9 alpha-difluoro-11 beta,17 alpha,21-trihydroxy-16 alphamethylpregna-1,4-diene-3,20-dione-17,21-methyl orthoacetate (0.42 g).

(b) The intermediate 17,21-orthoacetate of part (a) (150 mg) is dissolved in a solution of ethanol (10 ml) and aqueous 37% formaldehyde (2.5 ml), and treated with sodium bicarbonate (50 mg) at 80° C. for 16 hours under nitrogen atmosphere. The reaction mixture is poured into ice-water and the resulting precipitate collected by filtration and water washed. The crude material is subjected to preparative thin layer chromatography (2% methanol/chloroform) from which is isolated a material identified as the captioned 21-methylene adduct (75 mg, m.p. 218°–222° C. from acetone/hexane).

Similarly prepared, but substituting other orthoesters, e.g., triethyl orthopropionate, trimethyl ortho-n-butyrate and trimethyl ortho-n-pentanoate, for trimethyl orthoacetate are the following:

6 alpha,9 alpha-difluoro-11 beta,17 alpha,21-trihydroxy-16 alpha-methyl-21-methylenepregna-1,4-diene-3,20-dione-17,21-ethyl orthopropionate, m.p. 234°–237° C.;

6 alpha,9 alpha-difluoro-11 beta,17 alpha,21-trihydroxy-16 alpha-methyl-21-methylenepregna-1,4-diene-3,20-dione-17,21-methyl ortho-n-butyrate; and 6 alpha,9 alpha-difluoro-11 beta,17 alpha,21-trihydroxy-16 alpha-methyl-21-methylenepregna-1,4-diene-3,20-dione-17,21-methyl ortho-n-pentanoate.

Similarly prepared but substituting 6 alpha, 9 alpha-difluoro-11 beta, 17 alpha, 21-trihydroxy-16 alpha-methyl-pregna-1,4-diene-3,20-dione-17,21-acetonide for the ortho-acetate of Example 1(a) is 6 alpha, 9 alpha-difluoro-11 beta, 17 alpha, 21-trihydroxy-16 alpha-methyl-21-methylenepregna-1,4-diene-3,20-dione-17,21-acetonide, m.p. 223°–226° (dec.).

EXAMPLE 2

6 Alpha,9 alpha-difluoro-11 beta,16 alpha,17 alpha,21-tetrahydroxy-21-methylenepregna-1,4-diene-3,20-dione-16,17-acetonide-21-methyl ether.

Potassium bicarbonate (250 mg) is added to a solution of 6 alpha,9 alpha-difluoro-11 beta,16 alpha,17 alpha,21-tetrahydroxypregna-1,4-diene-3,20-dione-16,17-acetonide-21-methyl ether (fluocinolone acetonide 21-methyl ether) (250 mg) in ethanol (20 ml) and formalin (10 ml). The mixture is heated under nitrogen at 90°–100° C. for 16 hours, after which some of the solvent is removed by evaporation and water added. The crude product is filtered, dried and purified by preparative thin layer chromatography, twice developing with 3% methanol in chloroform. Thus, 115 mg., m.p. 235°–242° C. of the captioned product is obtained.

Similarly prepared but using other pregnadiene-21-alkyl or cycloheteroalkyl ethers are the following compounds:

6-alpha,9 alpha-difluoro-11 beta,16 alpha,17 alpha,21-tetrahydroxy-21-methylenepregna-1,4-diene-3,20-dione-16,17-acetonide-21-ethyl ether;

6 alpha,9 alpha-difluoro-11 beta,16 alpha,17 alpha,21-tetrahydroxy-21-methylenepregna-1,4-diene-3,20-dione-16,17-acetonide-21-n-propyl ether;

6 alpha,9 alpha-difluoro-11 beta,16 alpha,17 alpha,21-tetrahydroxy-21-methylenepregna-1,4-diene-3,20-dione-16,17-acetonide-21-n-butyl ether; and 6 alpha,9 alpha-difluoro-11 beta,16 alpha,17 alpha,21-tetrahydroxy-21-methylenepregna-1,4-diene-3,20-dione-16,17-acetonide-21-tetrahydropyran-2-yl ether, m.p. 208°–210°, freezes, remelts 280°–285°.

EXAMPLE 3

6 Alpha,9 alpha-difluoro-11 beta,17 alpha-dihydroxy-16 alpha,21-dimethylpregna-1,4-diene-3,20,21-trione-17-acetate.

A solution of 6 alpha,9 alpha-difluoro-11 beta,17 alpha,21-trihydroxy-16 alpha-methyl-21-methylenepregna-1,4-diene-3,20-dione-17,21-methyl orthoacetate (Example 1) (650 mg) in 40 ml of 50% aqueous acetic acid is heated to 90° C. for one hour under a nitrogen atmosphere. After most of the acetic acid is evaporated, water is added and the mixture allowed to cool in ice. The resulting solid crude product is collected by filtration, washed with water and vacuum dried. This material is subjected to preparative thin layer chromatography, eluting with 2.5% methanol/chloroform. After recrystallization of the recovered material from acetone/hexane, 370 mg of the captioned product is obtained (m.p. 300° C.).

Substitution of the other orthoesters illustrated in Example 1 for the orthoacetate in the above reaction affords the following compounds:

6 alpha,9 alpha-difluoro-11 beta,17 alpha-dihydroxy-16-alpha,21-dimethylpregna-1,4-diene-3,20,21-trione-17-propionate;

6 alpha,9 alpha-difluoro-11 beta,17 alpha-dihydroxy-16-alpha,21-dimethylpregna-1,4-diene-3,20,21-trione-17-n-butyrate; and 6 alpha,9 alpha-difluoro-11 beta,17 alpha-dihydroxy-16-alpha,21-dimethylpregna-1,4-diene-3,20,21-trione-17-n-pentanoate.

Substitution of the 16-methyl-17,21-acetonide (Example 1) for the 17,21-orthoacetate in the above reaction affords.

6 alpha,9 alpha-difluoro-11 beta,17 alpha-dihydroxy-16 alpha,21-dimethylpregna-1,4-diene-3,20,21-trione, m.p. 189°–193°.

EXAMPLE 4

6 Alpha,9 alpha-difluoro-11 beta,16 alpha,17 alpha-trihydroxy-21-methylpregna-1,4-diene-3,20,21-trione-16,17-acetonide.

6 Alpha,9 alpha-difluoro-11 beta,16 alpha,17 alpha,21-tetrahydroxy-21-methylenepregna-1,4-diene-3,20-dione-16,17-acetonide-21-tetrahydropyran-2-yl ether (40 mg) (Example 3) is dissolved in ethanol (5 ml) and 20 mg of para-toluene-sulfonic acid monohydrate is added. After one hour stirring at room temperature, water is added and the ethanol removed by vacuum distillation. The captioned product (crude) is filtered off, washed with water and vacuum dried. The product is purified by preparative thin layer chromatography (12% acetone in benzene), yielding 10 mg of the pure product, (m.p. 299°–301° C.).

The above captioned compound is also prepared using the 6 alpha,9 alpha-difluoro-11 beta,16 alpha,17 alpha,21-tetrahydroxy-21-methylpregna-1,4-diene-3,20-dione-16,17-acetonide-21-alkyl or cycloheteroalkyl ethers shown in Example 2 as substrate in this procedure.

EXAMPLE 6

21a-chloro-6 alpha,9 alpha-difluoro-11 beta,17 alpha-dihydroxy-16 alpha,21-dimethylpregna-1,4-diene-3,20,21-trione-17-acetate.

A freshly prepared mixture of 5% aqueous sodium hypochlorite (1 ml), t-butanol (2 ml) and 1 N sulfuric acid (2 ml) is added to a solution of 6 alpha,9 alpha-difluoro-11 beta,17 alpha,21-trihydroxy-16 alpha-methyl-21-methylenepregna-1,4-diene-3,20-dione-17,21-methyl orthoacetate (Example 1) (125 mg) in t-butanol (3 ml). After 10 minutes, water is added and the product filtered and dried. After preparative thin layer chromatography (twice developed in 12.5% acetone in benzene) 48 mg of pure 21a-chloro-6 alpha,9 alpha-difluoro-11 beta,17 alpha-dihydroxy-16 alpha,21-dimethylpregna-1,4-diene-3,20,21-trione-17-acetate is obtained, m.p. 260°–261° C.

Substitution of the other 17,21-orthoesters illustrated in Example 1 for the orthoacetate in the above reaction affords the following compounds:

21a-chloro-6 alpha,9 alpha-difluoro-11 beta,17-alpha-dihydroxy-16 alpha,21-dimethylpregna-1,4-diene-3,20-trione-17-propionate;

21a-chloro-6 alpha,9 alpha-difluoro-11 beta,17 alpha-dihydroxy-16 alpha,21-dimethylpregna-1,4-diene-3,20,21-trione-17-n-butyrate; and 21a-chloro-6 alpha,9 alpha-difluoro-11 beta,17 alpha-dihydroxy-16 alpha,21-dimethylpregna-1,4-diene-3,20,21-trione-17-n-pentanoate.

Substitution of the 16,17-acetonides illustrated in Example 2 for the orthoacetate in the above reaction affords 21a-chloro-6 alpha,9 alpha-difluoro-11 beta,16 alpha,17 alpha-trihydroxy-21-methylpregna-1,4-diene-3,20,21-trione-16,17-acetonide, m.p. 228°–233° (dec).

Substitution of the 17,21-acetonide of Example 1 for the above 17,21-orthoacetate affords 21a-chloro-6 alpha, 9 alpha-difluoro-11 beta, 17 alpha-dihydroxy-16,21-dimethyl-pregna-1,4-diene-3,20,21-trione, m.p. 206°–207°.

EXAMPLE 7

21a-bromo-6 alpha,9 alpha-difluoro-11 beta,17 alpha-dihydroxy-16 alpha,21-dimethylpregna-1,4-diene-3,20,21-trione-17-acetate.

N-bromosuccinimide (239 mg) in t-butanol (15 ml) and aqueous 1 N sulfuric acid (12 ml) is added to a solution of 6 alpha,9 alpha-difluoro-11 beta,17 alpha,21-trihydroxy-16-alpha-methyl-21-methylenepregna-1,4-diene-3,20-dione-17,21-methyl orthoacetate (Example 1) in t-butanol (15 ml). Water (200 ml) is added after ten minutes and, after cooling, the captioned crude product is filtered off. It is purified by preparative thin layer chromatography (twice developed in 2% methanol in chloroform) followed by crystallization from acetone/hexane, m.p. 232°–234° C. (dec.).

Substitution of the other 17,21-orthoesters illustrated in Example 1 for the orthoacetate in the above reaction affords the following compounds:

21a-bromo-6 alpha,9 alpha-difluoro-11 beta,17 alpha-dihydroxy-16 alpha,21-dimethylpregna-1,4-diene-3,20,21-trione-17-propionate;

21a-bromo-6 alpha,9 alpha-difluoro-11 beta,17 alpha-dihydroxy-16 alpha,21-dimethylpregna-1,4-diene-3,20,21-trione-17-n-butyrate; and 21a-bromo-6 alpha,9 alpha-difluoro-11 beta,17 alpha-dihydroxy-16 alpha,21-dimethylpregna-1,4-diene-3,20,21-trione-17-n-pentanoate.

Substitution of the 16,17-acetonides illustrated in Example 2 for the 17,21-orthoacetate in the above reaction affords 21a-bromo-6 alpha,9 alpha-difluoro-11 beta,16 alpha,17 alpha-trihydroxy-21-methylpregna-1,4-diene-3,20,21-trione-16,17-acetonide.

Substitution of the 17,21-acetonide of Example 1 for the above 17,21-orthoacetate affords 21a-bromo-6 alpha, 9 alpha-difluoro-11 beta, 17 alpha-dihydroxy-16,21-dimethylpregna-1,4-diene-3,20,21-trione.

EXAMPLE 8

21a-chloro-6 alpha,9 alpha-difluoro-11 beta,17 alpha,21-trihydroxy-16 alpha,21-dimethylpregna-1,4-diene-3,20-dione-17-acetate, Epimer B.

To 21a-chloro-6 alpha,9 alpha-difluoro-11 beta,17 alpha-dihydroxy-16 alpha,21-dimethylpregna-1,4-diene-3,20,21-trione-17-acetate (155 mg) (Example 6) in a methylene chloride/methanol mixture (2:1, 15 ml) at −20° C. is added sodium borohydride (5 mg) in methanol (1 ml), 30 minutes reaction time. After adding a few drops of acetic acid to destroy excess reagent, the solvents are removed by distillation and the residue taken up in ethyl acetate. After aqueous wash and drying of the solution, the solvent is removed. The pure captioned compound is obtained by preparative thin layer chromatography (4% methanol in chloroform), m.p. 242°–244° C. (dec).

Similarly prepared, using the 3,20,21-triones of Examples 4–7, are the following:

21a-chloro-6 alpha,9 alpha-difluoro-11 beta,17 alpha,21-trihydroxy-16 alpha,21-dimethylpregna-1,4-diene-3,20-dione-17-propionate;

21a-chloro-6 alpha,9 alpha-difluoro-11 beta,17 alpha, 21-trihydroxy-16 alpha,21-dimethylpregna-1,4-diene-3,20 dione-17-n-butyrate;

21a-chloro-6 alpha,9 alpha-difluoro-11 beta,17 alpha, 21-trihydroxy-16 alpha,21-dimethylpregna-1,4-diene-3,20-dione-17-n-pentanoate;

21a-bromo-6 alpha,9 alpha-difluoro-11 beta,17 alpha, 21-trihydroxy-16 alpha,21-dimethylpregna-1,4-diene-3,20-dione-17-n-pentanoate;

21a-bromo-6 alpha,9 alpha-difluoro-11 beta,17 alpha, 21-trihydroxy-16 alpha,21-dimethylpregna-1,4-diene-3,20-dione-17-n-butyrate;

21a-bromo-6 alpha,9 alpha-difluoro-11 beta,17 alpha, 21-trihydroxy-16 alpha,21-dimethylpregna-1,4-diene-3,20-dione-17-acetate;

6 alpha,9 alpha-difluoro-11 beta,17 alpha,21-trihydroxy-16 alpha-21-dimethylpregna-1,4-diene-3,20-dione-17-acetate, Epimer B, m.p. 232°–236°, freezes, remelts 261°–267°;

6 alpha,9 alpha-difluoro-11 beta,17 alpha,21-trihydroxy-16 alpha,21-dimethylpregna-1,4-diene-3-20-dione-17-n-butyrate;

6 alpha,9 alpha-difluoro-11 beta,17 alpha,21-trihydroxy-16 alpha,21-dimethylpregna-1,4-diene-3-20-dione-17-n-pentanoate;

21a-chloro-6 alpha,9 alpha-difluoro-11 beta,16 alpha,17 alpha,21-tetrahydroxy-21-methylpregna-1,4-diene-3,20-dione-16,17-acetonide;

21a-bromo-6 alpha,9 alpha-difluoro-11 beta,16 alpha,17 alpha,21-tetrahydroxy-21-methylpregna-1,4-diene-3,20-dione-16,17-acetonide; and 6 alpha,9 alpha-difluoro-11 beta-16 alpha,17 alpha,21-tetrahydroxy-21-methylpregna-1,4-diene-3,20-dione-16,17-acetonide, m.p. 234°–238°; and 6 alpha,9 alpha-difluoro-11 beta,17 alpha,21-trihydroxy-16,21-dimethylpregna-1,4-diene-3,20-dione, Epimer A, m.p. 214°–218°; Epimer B, m.p. 196°–197°.

EXAMPLE 9

6 Alpha,9 alpha-difluoro-11 beta,17 alpha,21a-trihydroxy-16 alpha,21-dimethylpregna-1,4-diene-3,20,21-trione-17,21a-bis-acetate.

Sodium acetate (250 mg) is added to a solution of the captioned 21a-bromo-17-acetoxy compound of Example 7 (140 mg) in dimethylformamide (10 ml) and the mixture allowed to stand overnight at room temperature. After dilution with water, the product is extracted with ethyl acetate which is then washed with water, dried with sodium sulfate and removed by vacuum distillation. 20 mg of the pure captioned compound is obtained by preparative thin layer chromatography of the residue developing three times with 3.5% methanol in chloroform followed by crystallization from acetone-hexane, m.p. 240°–242° C. (dec).

Substitution of the other 17-esters illustrated in Example 7 for the 17-acetoxy compound in the above reaction affords the following compounds:

6 alpha,9 alpha-difluoro-11 beta,17 alpha,21a-trihydroxy-16 alpha,21-dimethypregna-1,4-diene-3,20,21-trione-17-propionate-21a-acetate;

6 alpha,9 alpha-difluoro-11 beta,17 alpha,21a-trihydroxy-16 alpha,21-dimethylpregna-1,4-diene-3,20,21-trione-17-n-butyrate-21a-acetate; and 6 alpha,9 alpha-difluoro-11 beta,17 alpha,21a-trihydroxy-16 alpha,21-dimethylpregna-1,4-diene-3,20,21-trione-17-n-pentanoate-21a-acetate.

Substitution of the 16,17-acetonide prepared as illustrated in Example 7 for the 17-acetate of the above reaction affords 6 alpha,9 alpha-difluoro-11 beta,16 alpha,17 alpha,21a-tetrahydroxy-21-methylpregna-1,4-diene-3,20,21-trione-16,17-acetonide-21a-acetate.

By substituting other carboxylic acid salts for the sodium acetate in the above reaction, other 21-esters are prepared. For example, substitution of sodium propionate for sodium acetate yields 6 alpha, 9 alpha-difluoro-11 beta,17 alpha,21a-trihydroxy-16 alpha,21-dimethylpregna-1,4-diene-3,20,21-trione-17-acetate-21a-propionate.

EXAMPLE 10

21a-chloro-6 alpha,9 alpha-difluoro-11 beta,17 alpha,21-trihydroxy-16 alpha,21-dimethylpregna-1,4-diene-3,20-dione-17,21-bis-acetate, Epimer B.

21a-chloro-6 alpha,9 alpha-difluoro-11 beta 17 alpha,21-trihydroxy-16 alpha,21-dimethylpregna-1,4-diene-3,20-dione-17 acetate (130 mg), Example 8, is dissolved in a mixture of pyridine (4 ml) and acetic anhydride (1 ml). After one hour, ice water is added and the precipitated product washed and dried. The captioned material is purified by preparative thin layer chromatography (1.5% methanol in chloroform), m.p. 224°–229° C.

Similarly prepared using the other esters illustrated in Example 8 are the following:

21a-chloro-6 alpha,9 alpha-difluoro-11 beta,17 alpha,21-trihydroxy-16 alpha,21-dimethylpregna-1,4-diene-3,20-dione-17-propionate-21-acetate;

21a-chloro-6 alpha,9 alpha-difluoro-11 beta,17 alpha,21-trihydroxy-16 alpha,21-dimethylpregna-1,4-diene-3,20-dione-17-n-butyrate-21-acetate;

21a-chloro-6 alpha,9 alpha-difluoro-11 beta,17 alpha,21-trihydroxy-16 alpha,21-dimethylpregna-1,4-diene-3,20-dione-17-n-pentanoate-21-acetate;

6 alpha,9 alpha-difluoro-11 beta,17 alpha,21-trihydroxy-16 alpha,21-dimethylpregna-1,4-diene-3,20-dione-17,21-bis-acetate, Epimer B, m.p. 237°–239°;

21a-chloro-6 alpha,9 alpha-difluoro-11 beta,16 alpha,17 alpha,21-tetrahydroxy-21-methylpregna-1,4-diene-3,20-dione-16,17-acetonide-21-acetate;

6 alpha,9 alpha-difluoro-11 beta,16 alpha,17 alpha,21-tetrahydroxy-21-methylpregna-1,4-diene-3,20-dione-16,17-acetonide-21-acetate, Epimer A, m.p. 288°–293°; and Epimer B, m.p. 193°–197°, freezes, remelts 240°–242°.

By substituting other organic aliphatic anhydrides or acid chlorides for acetic anhydride in the above reaction other 21-esters are prepared. For example, replacing acetic anhydride with n-butyroyl chloride affords 21a-chloro-6 alpha,9 alpha-difluoro-11 beta,17 alpha,21-trihydroxy-16 alpha,21-dimethylpregna-1,4-diene-3,20-dione-17-acetate-21-n-butyrate.

EXAMPLE 11

6 Alpha,9 alpha-difluoro-11 beta,17 alpha,21,21a-tetrahydroxy-16 alpha,21-dimethylpregna-1,4-diene-3,20-dione-17,21-methyl orthoacetate-21a-acetate.

(a) Flumethasone (1 g) is warmed with p-toluene-sulfonic acid (300 mg) and trimethyl orthoacetate (20 ml) in benzene solution as detailed in Example 1, affording pure 6 alpha,9 alpha-difluoro-11 beta,17 alpha,21-trihydroxy-16 alpha-methylpregna-1,4-diene-3,20-dione-17,21-methyl orthoacetate in 85% w/w yield.

(b) 6 Alpha,9 alpha-difluoro-11 beta,17 alpha,21-trihydroxy-16 alpha-methylpregna-1,4-diene-3,20-dione-17,21-methyl orthoacetate (part a) (820 mg) and sodium bicarbonate (400 mg) in methanol (50 ml) and formalin (50 ml) are heated at 65° C. for 12 hours. Water is added and most of the methanol removed. The crude solid product is filtered off and dried. The product, 6 alpha,9 alpha-difluoro-11 beta,17 alpha,21,21a-tetrahydroxy-16 alpha,21-dimethylpregna-1,4-diene-3,20-dione-17,21-methyl orthoacetate, is purified by preparative thin layer chromatography (3% methanol in chloroform, twice developed) and crystallization from acetone/hexane mixture, m.p. 293°–296° C.

(c) 6 Alpha,9 alpha-difluoro-11 beta,17 alpha,21,21a-tetrahydroxy-16 alpha,21-dimethylpregna-1,4-diene-3,20-dione-17,21-methyl orthoacetate (part b) (175 mg) is reacted for 15 hours with acetic anhydride (1 ml) in pyridine (5 ml). The reaction mixture is poured into water, and extracted with ethyl acetate. The extract is dried with sodium sulfate and the solvent removed by evaporation. The captioned product is obtained by preparative thin layer chromatography (3% methanol in chloroform, thrice developed), m.p. 178°–184° C.

Substitution of other orthoesters, i.e., triethyl orthopropionate, trimethyl ortho-n-butyrate and trimethyl ortho-n-pentanoate, for the trimethyl orthoacetate in the above Example, affords the following compounds:

6 alpha,9 alpha-difluoro-11 beta,17 alpha,21,21a-tetrahydroxy-16 alpha,21-dimethylpregna-1,4-diene-3,20-dione-17,21-ethyl orthopropionate-21a-acetate;

6 alpha,9 alpha-difluoro-11 beta,17 alpha,21,21a-tetrahydroxy-16 alpha,21-dimethylpregna-1,4-diene-3,20-dione-17,21-methyl ortho-n-butyrate-21a-acetate; and 6 alpha,9 alpha-difluoro-11 beta,17 alpha,21,21a-tetrahydroxy-16 alpha,21-dimethylpregna-1,4-diene-3,20-dione-17,21-methyl ortho-n-pentanoate-21a-acetate.

Substitution of other organic aliphatic anhydrides or acid chlorides for the acetic anhydride in the above illustrative Example affords other 21a-esters. For example, replacing acetic anhydride with propionyl chloride yields 6 alpha,9 alpha-difluoro-11 beta,17 alpha,21,21a-tetrahydroxy-16 alpha,21-dimethylpregna-1,4-diene-3,20-dione-17,21-methyl orthoacetate-21a-propionate.

EXAMPLE 12

6 Alpha,9 alpha-difluoro-11 beta,17 alpha,21-trihydroxy-16 alpha,21-dimethylpregna-1,4-diene-3,20-dione-17,21-methyl orthoacetate (Epimer A).

A solution of 6 alpha,9 alpha-difluoro-11 beta,17 alpha,21-trihydroxy-16 alpha,21-dimethylpregna-1,4-diene-3,20-dione (Epimer A) (190 mg) (Example 8) and para-toluenesulfonic acid monohydrate (40 mg) in trimethyl orthoacetate (10 ml) and benzene (30 ml) is slowly distilled (75° bath) to remove water azeotropically until thin layer chromatography indicates the reaction to be complete. Most remaining solvent is then removed by vacuum distillation. Ethyl acetate is added to the residue, and the solution is washed with dilute sodium bicarbonate, followed by water. After the solution is dried over sodium sulfate and then evaporated to dryness, the crude product is purified by preparative thin layer chromatography (3% methanol/chloroform). Thus, after crystallization from acetone-hexane, 100 mg of the captioned product is obtained (m.p 210°–211°).

Similarly prepared, but using Epimer B (Example 8) of the 21-methyl-11,17,21-triol starting material in the above reaction, is obtained Epimer B of the captioned product.

Similarly prepared but substituting other orthoesters, i.e. triethyl orthopropionate, trimethyl ortho-n-butyrate, and trimethyl ortho-n-pentanoate for trimethyl orthoacetate in the above reaction are the following:

6 alpha,9 alpha-difluoro-11 beta,17 alpha,21-trihydroxy-16 alpha,21-dimethylpregna-1,4-diene-3,20-dione-17,21-ethyl orthopropionate;

6 alpha,9 alpha-difluoro-11 beta,17 alpha,21-trihydroxy-16 alpha,21-dimethylpregna-1,4-diene-3,20-dione-17,21-methyl ortho-n-butyrate; and 6 alpha,9 alpha-difluoro-11 beta,17 alpha,21-trihydroxy-16 alpha,21-dimethylpregna-1,4-diene-3,20-dione-17,21-methyl ortho-n-pentanoate.

EXAMPLE 13

21-Chloro-6 alpha,9 alpha-difluoro-11 beta,17 alpha-dihydroxy-16 alpha,21-dimethylpregna-1,4-diene-3,20-dione-17-acetate (Epimer A)

A solution of trityl chloride (400 mg) in methylene chloride (5 ml) is added to 6 alpha,9 alpha-difluoro-11 beta,17 alpha,21-trihydroxy-16 alpha,21-dimethylpregna-1,4-diene-3,20-dione-17,21-methyl orthoacetate (Epimer B) (110 mg) (Example 12). After warming at 40° C. for one hour, the solvent is removed, the residue applied for preparative TLC plates, and developed twice in 2% methanol in chloroform. The purified above-captioned product thereby obtained is crystallized from acetone/hexane, m.p. 243°–246° C.

Similarly prepared using the other 21-methyl-17,21-orthoesters illustrated in Example 12 are the following:

21-chloro-6 alpha,9 alpha-difluoro-11 beta, 17 alpha-dihydroxy-16 alpha,21 dimethylpregna-1,4-diene-3,20-dione-17-propionate m.p. 225°–227° decompose;

21-chloro-6 alpha,9 alpha-difluoro-11 beta, 17 alpha-dihydroxy-16 alpha,21-dimethylpregna-1,4-diene-3,20-dione-17-n-butyrate; and 21-chloro-6 alpha,9 alpha-difluoro-11 beta, 17 alpha-dihydroxy-16 alpha,21-dimethylpregna-1,4-diene-3,20-dione-17-n-pentanoate.

Substitution of trityl bromide for trityl chloride in the above example yields 21-bromo-6 alpha,9 alpha-difluoro-11 beta,17 alpha-dihydroxy-16 alpha,21-dimethylpregna-1,4-diene-3,20-dione-17-acetate.

EXAMPLE 14

21-Chloro-6 alpha,9 alpha-difluoro-11 beta,16 alpha,17 alpha-trihydroxy-21-methylpregna-1,4-diene-3,20-dione 16,17-acetonide (a) A solution of 6 alpha,9 alpha-difluoro-11 beta, 16 alpha,17 alpha,21-tetrahydroxy-21-methylpregna-1,4-diene-3,20-dione-16,17-acetonide (123 mg) in pyridine (3 ml) is reacted with methane sulfonyl chloride (0.1 ml) at 0° C. After 10 minutes the reaction mixture is poured into ice water and extracted with chloroform. The chloroform solution of crude 21-mesyloxy-6 alpha,9 alpha-difluoro-11 beta, 16 alpha,17 alpha-trihydroxy-21-methylpregna-1,4-diene-3,20-dione-16,17-acetonide is washed with ice-water, dried with sodium sulfate and vacuum distilled to remove solvents, affording the crude solid.

(b) Lithium chloride (500 mg) is added to a solution of the 21-mesyloxy-6 alpha,9 alpha-difluoro-11 beta, 16 alpha,17 alpha-trihydroxy-21-methylpregna-1,4-diene-3,20-dione-16,17-acetonide of step (a) in dimethylformamide (5 ml). After heating for two hours at 130° C., some dimethylformamide is removed by distillation and the reaction mixture poured into ice water. The captioned product is filtered off, washed with water and dried under vacuum. The resulting mixture of C-21 epimers is separated by preparative thin layer chromatography (15% acetone in benzene); 44 mg, Epimer B, m.p. 300+°C. (dec.); 47 mg, Epimer A, m.p. 300+°C. (dec.)

By substituting other halide salts for lithium chloride in the above reaction, other 21-halides are prepared. For example, substitution of lithium bromide for lithium chloride yields 21-bromo-6 alpha,9 alpha-difluoro-11 beta,16 alpha,17 alpha-trihydroxy-21-methylpregna-1,4-diene-3,20-dione-16,17-acetonide.

EXAMPLE 15

6 Alpha, 9 alpha-difluoro-11 beta, 16 alpha, 17 alpha-trihydroxy-21-methylpregna-1,4-diene-3,20,21-trione-16,17-acetonide In a 200 ml flask, 470 mg of 6 alpha, 9 alpha-difluoro-11 beta, 16 alpha, 17 alpha-trihydroxypregna-1,4-diene-3,20-dione-21-aldehyde hydrate is heated at 110° under high vacuum (0.1 mm Hg) for 1 hour, thereby releasing the free aldehyde. The aldehyde is slurried in 100 ml of dry ether at room temperature and 25 ml of a solution of diazomethane in ether (prepared from 0.5 g of N- nitrosomethyl urea by standard procedures) is added. The resulting solution is allowed to stir for two days, after which the reaction is judged complete by TLC. The reaction mixture is evaporated to dryness and the residue is recrystallized three times from acetone-hexane, affording 200 mg of the pure captioned product, m.p. 299°–301°.

What is claimed is:

1. A compound of the formula

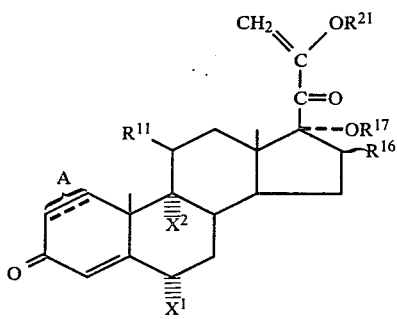

wherein
$R^{11}$ is chloro or hydroxy;
$X^1$ and $X^2$ independently are halo selected from the group chloro and fluoro;
$R^{16}$ is methyl;
$R^{17}$ independently is hydrogen, benzoyl or $C_2$ to $C_6$ linear or branched acyl; or
$R^{16}$ and $OR^{17}$ taken together are the radical

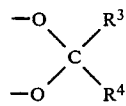

where $R^3$ hydrogen, $C_1$ to $C_5$ linear or branched alkyl, phenyl and $R^4$ is the same or different than $R^3$ as defined above or is $C_1$ to $C_6$ linear or branched alkoxy or $R^3$ and $R^4$ taken together with the carbon atom of said radical are $C_5$ to $C_{10}$ cycloalkyl or $C_4$ to $C_9$ heterocyclic alkyl having one heterocyclic atom selected from the group oxygen, nitrogen and sulfur optionally substituted with methyl or ethyl;
$R^{21}$ independently is $C_1$ to $C_6$ linear or branched alkyl or $C_4$ to $C_9$ heterocyclic alkyl having one heterocyclic atom selected from the group oxygen, nitrogen and sulfur optionally substituted with methyl or ethyl; or
$OR^{17}$ and $OR^{21}$ taken together are the radical

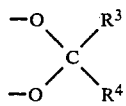

where $R^3$ is defined above and $R^4$ is $C_1$ to $C_6$ linear or branched alkoxy;
and A is a single or double bond.

2. The compound of claim 1 wherein $OR^{17}$ and $OR^{21}$ are taken together and are the radical

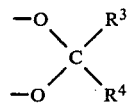

where $R^3$ is $C_1$ to $C_4$ linear or branched alkyl and $R^4$ is $C_1$ to $C_4$ linear or branched alkoxy.

3. The compound of claim 2 wherein $R^3$ is methyl, $R^4$ is methoxy, $R^{11}$ is hydroxy, $X^1$ and $X^2$ are fluoro and A is a double bond.

4. The compound of claim 2 wherein $R^3$ is ethyl, $R^4$ is ethoxy, $R^{11}$ is hydroxy, $X^1$ and $X^2$ are fluoro and A is a double bond.

5. The compound of claim 1 wherein $R^{16}$ and $OR^{17}$ are taken together and are the radical

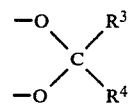

where $R^3$ and $R^4$ are the same and are $C_1$ to $C_4$ linear or branched alkyl.

6. The compound of claim 5 wherein $R^3$ and $R^4$ are the same and are methyl and $R^{21}$ is $C_1$ to $C_4$ linear or branched alkyl.

7. The compound of claim 6 wherein $R^{21}$ is methyl.

8. The compound of claim 5 wherein $R^3$ and $R^4$ are the same and are methyl and $R^{21}$ is tetrahydropyran-2-yl.

9. A compound of the formula

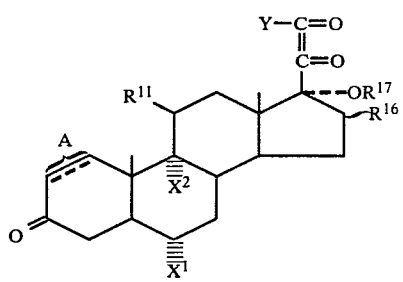

wherein
$R^{11}$ is chloro or hydroxy;
$X^1$ and $X^2$ independently are halo selected from the group chloro and fluoro;
$R^{16}$ is methyl;
$R^{17}$ independently is hydrogen, benzoyl or $C_2$ to $C_6$ linear or branched acyl;
$R^{16}$ and $OR^{17}$ taken together are the radical

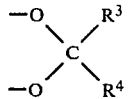

where $R^3$ is hydrogen, $C_1$ to $C_5$ linear or branched alkyl or phenyl and $R^4$ is the same or different than $R^3$ as defined above or is $C_1$ to $C_6$ linear branched alkoxy or $R^3$ and $R^4$ taken together with the carbon atom of said radical are $C_5$ to $C_{10}$ cycloalkyl or $C_4$ to $C_9$ heterocyclic alkyl having one heterocyclic atom selected from the group oxygen, nitrogen and sulfur optionally substituted with methyl or ethyl;

Y is selected from the group methyl, halomethyl and the radical —CH₂OC(O)R where R is C₁ to C₆ linear or branched alkyl; and A is a single or double bond; with the proviso that when R¹⁷ is hydrogen, Y is selected from the group halomethyl and the radical —CH₂OC(O)R where R is as previously defined.

10. The compound of claim 9 wherein X¹ and X² are fluoro, R¹¹ is hydroxy, R¹⁷ is C₂ to C₄ linear or branched acyl and R is methyl.

11. The compound of claim 10 wherein R¹⁷ is acetoxy and A is a double bond.

12. The compound of claim 9 wherein X¹ and X² are fluoro, R¹¹ is hydroxy, R¹⁶ and OR¹⁷ are taken together and are the radical

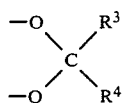

where R³ and R⁴ are the same and are C₁ to C₄ linear or branched alkyl and Y is methyl.

13. The compound of claim 12 wherein R³ and R⁴ are the same and are methyl and A is a double bond.

14. The compound of claim 9 wherein X¹ and X² are fluoro, R¹¹ is hydroxy, R¹⁶ and OR¹⁷ are taken together and are the radical

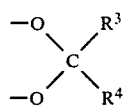

where R³ and R⁴ are the same and are C₁ to C₄ linear or branched alkyl and Y is halomethyl.

15. The compound of claim 14 wherein R³ and R⁴ are the same and are methyl, Y is chloromethyl and A is a double bond.

16. The compound of claim 9 wherein X¹ and X² are fluoro, R¹¹ is hydroxy, R¹⁶ and OR¹⁷ are taken together and are the radical

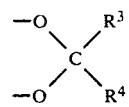

where R³ and R⁴ are the same and are C₁ to C₄ linear or branched alkyl, and Y is the radical —CH₂OC(O)R where R is C₁ to C₄ linear or branched alkyl.

17. The compound of claim 16 wherein R³ and R⁴ are the same and are methyl, Y is the radical —CH₂OC-(O)CH₃ and A is a double bond.

18. A compound of the formula

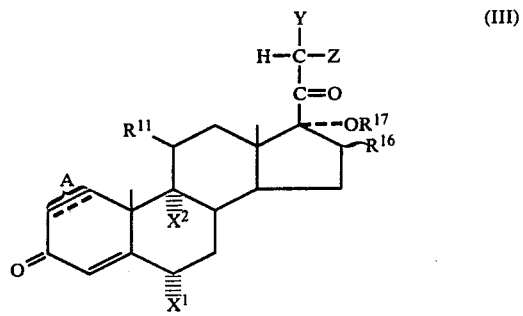

wherein
R¹¹ is chloro or hydroxy;
X¹ and X² independently are halo selected from the group chloro and fluoro;
R¹⁶ is methyl;
R¹⁷ independently is hydrogen, benzoyl or C₂ to C₆ linear or branched acyl or R¹⁶ and OR¹⁷ taken together are the radical

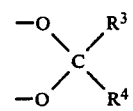

where R³ is hydrogen, C₁ to C₅ linear or branched alkyl or phenyl and R⁴ is the same or different than R³ as defined above or is C₁ to C₆ linear or branched alkoxy or R³ and R⁴ taken together with the carbon atom of said radical are C₅ to C₁₀ cycloalkyl or C₄ to C₉ heterocyclic alkyl having one heterocyclic atom selected from the group oxygen, nitrogen and sulfur optionally substituted with methyl or ethyl;
Y is selected from the group methyl, halomethyl and the radical —CH₂OC(O)R where R is C₁ to C₆ linear or branched alkyl; Z independently is C₂ to C₇ linear or branched acyloxy, hydroxy or halo or Z and OR¹⁷ taken together are the radical

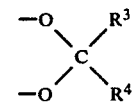

where R³ is defined above and R⁴ is C₁ to C₆ linear or branched alkoxy with the proviso that when Z independently is C₂ to C₇ linear or branched acyloxy or hydroxy, Y is selected from the group halomethyl and the radical —CH₂OC(O)R where R is as previously defined, with the further proviso that when Y is methyl Z is halo.

19. The compound of claim 18 wherein X¹ and X² are fluoro, R¹¹ is hydroxy, R¹⁷ is C₂ to C₅ linear or branched acyl, Y is halomethyl and Z is hydroxy.

20. The compound of claim 19 wherein R¹⁷ is acetoxy and A is a double bond.

21. The compound of claim 18 wherein X¹ and X² are fluoro, R¹¹ is hydroxy, R¹⁶ and OR¹⁷ are taken together and are the radical

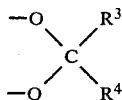

where $R^3$ and $R^4$ are the same and are $C_1$ to $C_4$ linear or branched alkyl, Y is halomethyl and Z is hydroxy.

22. The compound of claim 21 where $R^3$ and $R^4$ are methyl, Y is the group chloromethyl and A is a double bond.

23. The compound of claim 18 wherein $X^1$ and $X^2$ are fluoro, $R^{11}$ is hydroxy, $R^{17}$ is $C_2$ to $C_4$ linear branched acyl, Y is halomethyl and Z is $C_2$ to $C_4$ linear or branched acyloxy.

24. The compound of claim 23 wherein $R^{17}$ is acetyl, Z is acetoxy and A is a double bond.

25. The compound of claim 18 wherein $X^1$ and $X^2$ are fluoro, $R^{11}$ is hydroxy, $R^{16}$ and $OR^{17}$ are taken together and are the radical

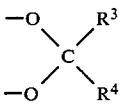

where $R^3$ and $R^4$ are the same and are $C_1$ to $C_4$ linear or branched alkyl, Y is halomethyl and Z is $C_2$ to $C_4$ linear or branched acyloxy.

26. The compound of claim 25 wherein $R^3$ and $R^4$ are methyl, Z is acetoxy and A is a double bond.

27. The compound of claim 18 wherein $X^1$ and $X^2$ are fluoro, $R^{11}$ is hydroxy, Y is methyl and Z and $OR^{17}$ are taken together and are the radical

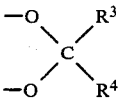

where $R^3$ is $C_1$ to $C_4$ linear or branched alkyl and $R^4$ is $C_1$ to $C_4$ linear or branched alkoxy.

28. The compound of claim 27 wherein $R^3$ is methyl, $R^4$ is methoxy and A is a double bond.

29. The compound of claim 18 wherein $X^1$ and $X^2$ are fluoro, $R^{11}$ is hydroxy, Y is methyl, Z is halo selected from the group chloro and bromo and $R^{17}$ is $C_2$ to $C_5$ linear or branched acyl.

30. The compound of claim 29 wherein Z is chloro, $R^{17}$ is acetyl and A is a double bond.

31. The compound of claim 29 wherein Z is chloro, $R^{17}$ is propionyl and A is a double cond.

32. The compound of claim 18 wherein $X^1$ and $X^2$ are fluoro, $R^{11}$ is hydroxy, Y is methyl, Z is halo selected from the group chloro and bromo and $R^{16}$ and $OR^{17}$ are taken together and are the radical

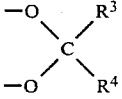

where $R^3$ and $R^4$ are the same and are $C_1$ to $C_4$ linear or branched alkyl.

33. The compound of claim 32 wherein Z is chloro, $R^3$ and $R^4$ are methyl and A is a double bond.

34. A pharmaceutical composition useful for treating inflammatory disorders comprising a pharmaceutically acceptable non-toxic carrier in admixture with an effective amount of a compound having the formula:

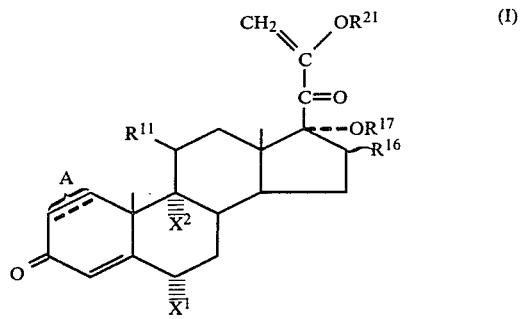

wherein $R^{11}$ is chloro or hydroxy;

$X^1$ and $X^2$ independently are halo selected from the group chloro and fluoro;

$R^{16}$ is methyl;

$R^{17}$ independently is hydrogen, benzoyl or $C_2$ to $C_6$ linear or branched acyl; or $R^{16}$ and $OR^{17}$ taken together are the radical

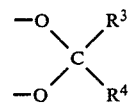

where $R^3$ is hydrogen, $C_1$ to $C_5$ linear or branched alkyl or phenyl and $R^4$ is the same or different than $R^3$ as defined above or is $C_1$ to $C_6$ linear or branched alkoxy or $R^3$ and $R^4$ taken together with the carbon atom of said radical are $C_5$ to $C_{10}$ cycloalkyl or $C_4$ to $C_9$ heterocyclic alkyl having one heterocyclic atom selected from the group oxygen, nitrogen and sulfur optionally substituted with methyl or ethyl;

$R^{21}$ independently is $C_1$ to $C_6$ linear or branched alkyl or $C_4$ to $C_9$ heterocyclic alkyl having one heterocyclic atom selected from the group oxygen, nitrogen and sulfur optionally substituted with methyl or ethyl; or $OR^{17}$ and $OR^{21}$ taken together are the radical

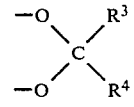

where $R^3$ is defined above and $R^4$ is $C_1$ to $C_6$ linear or branched alkoxy;

and A is a single or double bond.

35. A pharmaceutical composition useful for treating inflammatory disorders comprising a pharmaceutically acceptable non-toxic carrier in admixture with an effective amount of a compound having the formula:

(II)

wherein
$R^{11}$ is chloro or hydroxy;
$X^1$ and $X^2$ independently are halo selected from the group chloro and fluoro;
$R^{16}$ is methyl;
$R^{17}$ independently is hydrogen, benzoyl or $C_2$ to $C_6$ linear or branched acyl;
$R^{16}$ and $OR^{17}$ taken together are the radical $$\begin{array}{c} -O \\ \phantom{-}\diagdown \phantom{/} R^3 \\ \phantom{-}C \\ \phantom{-}\diagup \phantom{\diagdown} R^4 \\ -O \end{array}$$

where $R^3$ is hydrogen, $C_1$ to $C_5$ linear or branched alkyl or phenyl and $R^4$ is the same or different than $R^3$ as defined above or is $C_1$ to $C_6$ linear branched alkoxy or $R^3$ and $R^4$ taken together with the carbon atom of said radical are $C_5$ to $C_{10}$ cycloalkyl or $C_4$ to $C_9$ heterocyclic alkyl having one heterocyclic atom selected from the group oxygen, nitrogen and sulfur optionally substituted with methyl or ethyl;
Y is selected from the group methyl, halomethyl and the radical —CH$_2$OC(O)R where R is $C_1$ to $C_6$ linear or branched alkyl; and A is a single or double bond; with the proviso that when $R^{17}$ is hydrogen, Y is selected from the group halomethyl and the radical —CH$_2$OC(O)R where R is as previously defined.

36. A pharmaceutical composition useful for treating inflammatory disorders comprising a pharmaceutically acceptable non-toxic carrier in admixture with an effective amount of a compound having the formula:

(III)

wherein
$R^{11}$ is chloro or hydroxy;
$X^1$ and $X^2$ independently are halo selected from the group chloro and fluoro;
$R^{16}$ is methyl;
$R^{17}$ independently is hydrogen, benzoyl or $C_2$ to $C_6$ linear or branched acyl or $R^{16}$ and $OR^{17}$ taken together are the radical $$\begin{array}{c} -O \\ \phantom{-}\diagdown \phantom{/} R^3 \\ \phantom{-}C \\ \phantom{-}\diagup \phantom{\diagdown} R^4 \\ -O \end{array}$$

where $R^3$ is hydrogen, $C_1$ to $C_5$ linear or branched alkyl or phenyl and $R^4$ is the same or different than $R^3$ as defined above or is $C_1$ to $C_6$ linear or branched alkoxy or $R^3$ and $R^4$ taken together with the carbon atom of said radical are $C_5$ to $C_{10}$ cycloalkyl or $C_4$ to $C_9$ heterocyclic alkyl having one heterocyclic atom selected from the group oxygen, nitrogen and sulfur optionally substituted with methyl or ethyl;
Y is selected from the group methyl, halomethyl and the radical —CH$_2$OC(O)R where R is $C_1$ to $C_6$ linear or branched alkyl; Z independently is $C_2$ to $C_7$ linear or branched acyloxy, hydroxy or halo or Z and $OR^{17}$ taken together are the radical $$\begin{array}{c} -O \\ \phantom{-}\diagdown \phantom{/} R^3 \\ \phantom{-}C \\ \phantom{-}\diagup \phantom{\diagdown} R^4 \\ -O \end{array}$$

where $R^3$ is defined above and $R^4$ is $C_1$ to $C_6$ linear or branched alkoxy with the proviso that when Z independently is $C_2$ to $C_7$ linear or branched acyloxy or hydroxy, Y is selected from the group halomethyl and the radical —CH$_2$OC(O)R where R is as previously defined, with the further proviso that when Y is methyl Z is halo.

37. A method for relieving symptoms associated with inflammatory disorders comprising administering an effective amount of a compound having the formula:

(I)

wherein
$R^{11}$ is chloro or hydroxy;
$X^1$ and $X^2$ independently are halo selected from the group chloro and fluoro;
$R^{16}$ is methyl;
$R^{17}$ independently is hydrogen, benzoyl or $C_2$ to $C_6$ linear or branched acyl; or
$R^{16}$ and $OR^{17}$ taken together are the radical $$\begin{array}{c} -O \\ \phantom{-}\diagdown \phantom{/} R^3 \\ \phantom{-}C \\ \phantom{-}\diagup \phantom{\diagdown} R^4 \\ -O \end{array}$$

where $R^3$ is hydrogen, $C_1$ to $C_5$ linear or branched alkyl or phenyl and $R^4$ is the same or different than $R^3$ as defined above or is $C_1$ to $C_6$ linear or branched alkoxy or $R^3$ and $R^4$ taken together with the carbon atom of said radical are $C_5$ to $C_{10}$ cycloalkyl or $C_4$ to $C_9$ heterocyclic alkyl having one heterocyclic atom selected from the group oxygen, nitrogen and sulfur optionally substituted with methyl or ethyl;

$R^{21}$ independently is $C_1$ to $C_6$ linear or branched alkyl or $C_4$ to $C_9$ heterocyclic alkyl having one heterocyclic atom selected from the group oxygen, nitrogen and sulfur optionally substituted with methyl or ethyl; or $OR^{17}$ and $OR^{21}$ taken together are the radical

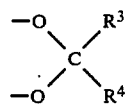

where $R^3$ is defined above and $R^4$ is $C_1$ to $C_6$ linear or branched alkoxy;
and A is a single or double bond.

38. A method for relieving symptoms associated with inflammatory disorders comprising administering an effective amount of the compound having a formula:

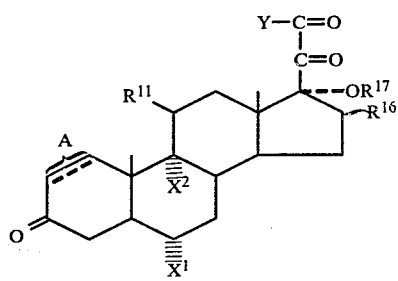

wherein
$R^{11}$ is chloro or hydroxy;
$X^1$ and $X^2$ independently are halo selected from the group chloro and fluoro;
$R^{16}$ is methyl;
$R^{17}$ independently is hydrogen, benzoyl or $C_2$ to $C_6$ linear or branched acyl;
$R^{16}$ and $OR^{17}$ taken together are the radical

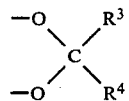

where $R^3$ is hydrogen, $C_1$ to $C_5$ linear or branched alkyl or phenyl and $R^4$ is the same or different than $R^3$ as defined above or is $C_1$ to $C_6$ linear branched alkoxy or $R^3$ and $R^4$ taken together with the carbon atom of said radical are $C_5$ to $C_{10}$ cycloalkyl or $C_4$ to $C_9$ heterocyclic alkyl having one heterocyclic atom selected from the group oxygen, nitrogen and sulfur optionally substituted with methyl or ethyl;
Y is selected from the group methyl, halomethyl and the radical —$CH_2OC(O)R$ where R is $C_1$ to $C_6$ linear or branched alkyl; and A is a single or double bond; with the proviso that when $R^{17}$ is hydrogen, Y is selected from the group halomethyl and the radical —$CH_2OC(O)R$ where R is as previously defined.

39. A method for relieving symptoms associated with inflammatory disorders comprising administering an effective amount of a compound having the formula:

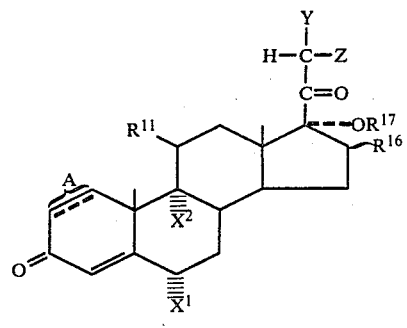

wherein
$R^{11}$ is chloro or hydroxy;
$X^1$ and $X^2$ independently are halo selected from the group chloro and fluoro;
$R^{16}$ is methyl;
$R^{17}$ independently is hydrogen, benzoyl or $C_2$ to $C_6$ linear or branched acyl or $R^{16}$ and $OR^{17}$ taken together are the radical

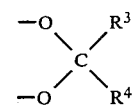

where $R^3$ is hydrogen, $C_1$ to $C_5$ linear or branched alkyl or phenyl and $R^4$ is the same or different than $R^3$ as defined above or is $C_1$ to $C_6$ linear or branched alkoxy or $R^3$ and $R^4$ taken together with the carbon atom of said radical are $C_5$ to $C_{10}$ cycloalkyl or $C_4$ to $C_9$ heterocyclic alkyl having one heterocyclic atom selected from the group oxygen, nitrogen and sulfur optionally substituted with methyl or ethyl;

Y is selected from the group methyl, halomethyl and the radical —$CH_2OC(O)R$ where R is $C_1$ to $C_6$ linear or branched alkyl; Z independently is $C_2$ to $C_7$ linear or branched acyloxy, hydroxy or halo or Z and $OR^{17}$ taken together are the radical

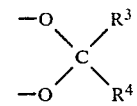

where $R^3$ is defined above and $R^4$ is $C_1$ to $C_6$ linear or branched alkoxy with the proviso that when Z independently is $C_2$ to $C_7$ linear or branched acyloxy or hydroxy, Y is selected from the group halomethyl and the radical —$CH_2OC(O)R$ where R is as previously defined, with the further proviso that when Y is methyl Z is halo.

40. A process for preparing a compound selected from the group represented by the formula

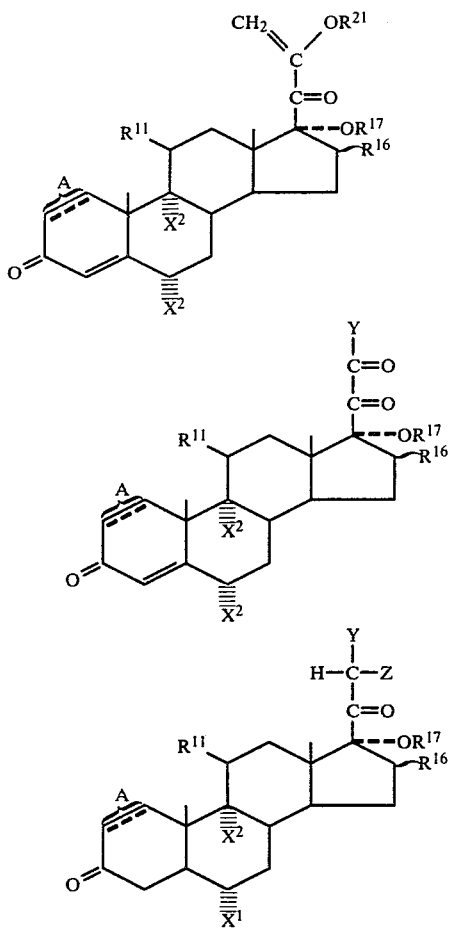

(I)

(II)

(III)

wherein
$R^{11}$ is chloro or hydroxy;
$X^1$ and $X^2$ independently are halo selected from the group chloro and fluoro;
$R^{16}$ is methyl;
$R^{17}$ independently is hydrogen, benzoyl or $R^{16}$ and $OR^{17}$ taken together are the radical

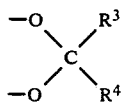

where $R^3$ is hydrogen, $C_1$ to $C_5$ linear or branched alkyl or phenyl and $R^4$ is the same or different than $R^3$ as defined above or is $C_1$ $C_6$ linear or branched alkoxy or $R^3$ and $R^4$ taken together with the carbon atom of said radical are $C_5$ to $C_{10}$ cycloalkyl or $C_4$ to $C_9$ heterocyclic alkyl having one heterocyclic atom selected from the group oxygen, nitrogen and sulfur optionally substituted with methyl or ethyl or $OR^{17}$ and $OR^{21}$ taken together are the radical

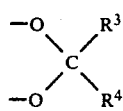

where $R^3$ is defined above and $R^4$ is $C_1$ to $C_4$ linear or branched alkoxy; Y is selected from the group methyl, halomethyl, and the radical —$CH_2OC(O)R$ where R is $C_1$ to $C_6$ linear or branched alkyl; Z independently is $C_1$ to $C_7$ linear or branched acyloxy, hydroxy or halo or Z and $OR^{17}$ taken together are the radical

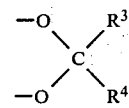

where $R^3$ and $R^4$ is defined above; and A is a double or single bond; which comprises (a) treating a compound of the formula

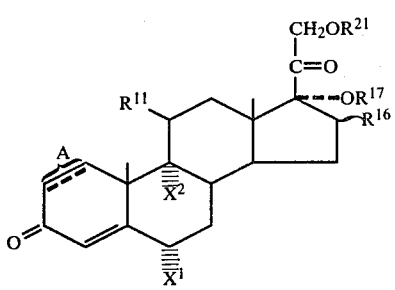

where $R^{11}$, $X^1$, $X^2$, $R^{16}$, $R^{17}$, $R^{21}$ and A are defined above, with formaldehyde in the presence of base to obtain the compound of Formula (I);

(b) treating the compound of Formula (I) with an aqueous solution of inorganic mineral or organic carboxylic acid to obtain the compound of Formula (II) where Y is methyl or alternatively treating the compound of Formula (I) with an aqueous solution of a halogen selected from the group chlorine and bromine to obtain the compound of Formula (II) where Y is halomethyl or, alternatively, treating the compound of Formula (II) where Y is halomethyl with a compound of the formula MOC(O)R where M is alkali or alkaline earth metal and R is defined above to obtain the compound of Formula (II) where Y is the radical —$CH_2OC(O)R$ where R is defined above;

(c) treating the compound of Formula (II) with sodium borohydride to obtain the compound of Formula (III) where Z is hydroxy;

(d) treating the compound of Formula (III) where Z is hydroxy with a $C_1$ to $C_6$ linear or branched organic carboxylic acid, and chloride or anhydride to obtain a compound of Formula (III) where Z is $C_2$ to $C_6$ linear or branched acyloxy or alternatively treating the compound of Formula (III) where Z is hydroxy consecutively with a sulfonic acid chloride and then with an alkali or alkaline earth metal halide to obtain a compound of Formula (III) where Z is halo;

(e) treating a compound of Formula (III) where Z and and $OR^{17}$ are taken together with a trityl halide to obtain a compound of Formula (III) where Z is halo.

41. A process for preparing the compounds of the formula

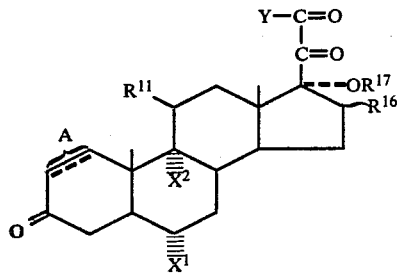

(II)

wherein $R^{11}$ is chloro or hydroxy; $X^1$ and $X^2$ independently are halo selected from the group chlorio and fluoro; $R^{16}$ is methyl
$R^{17}$ independently is hydrogen, benzoyl or $C_1$ to $C_6$ linear or branched acyl or $R^{16}$ and $OR^{17}$ taken together are the radical

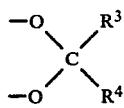

where $R^3$ is hydrogen, $C_1$ to $C_5$ linear or branched alkyl or phenyl and $R^4$ is the same or different than $R^3$ previously defined or is $C_1$ to $C_6$ linear or branched alkoxy or $R^3$ and $R^4$ taken together with the carbon atom of said radical are $C_4$ to $C_9$ heterocyclic alkyl having one heterocyclic atom selected from the group oxygen, nitrogen and sulfur optionally substituted with methyl or ethyl Y is methyl and A is a double or single bond comprising treating a compound of the formula

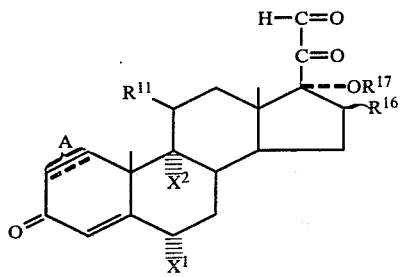

wherein $R^{11}$, $X^1$, $X^2$, $R^{16}$, $R^{17}$ and Z are as previously defined with diazomethane at about 0° to about 25° C. for from about 30 minutes to about 48 hours.

* * * * *